US010555670B2

(12) United States Patent
Das et al.

(10) Patent No.: US 10,555,670 B2
(45) Date of Patent: Feb. 11, 2020

(54) ADAPTIVE FILTRATION OF SWEAT ARTIFACTS DURING ELECTRONIC BRAIN MONITORING

(71) Applicant: International Business Machines Corporation, Armonk, NY (US)

(72) Inventors: Payel Das, Yorktown Heights, NY (US); Ryan Hubbard, Urbana, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 321 days.

(21) Appl. No.: 15/645,133

(22) Filed: Jul. 10, 2017

(65) Prior Publication Data
US 2019/0008383 A1 Jan. 10, 2019

(51) Int. Cl.
*A61B 5/00* (2006.01)

(52) U.S. Cl.
CPC .......... *A61B 5/0006* (2013.01); *A61B 5/4812* (2013.01); *A61B 5/721* (2013.01); *A61B 5/4064* (2013.01); *A61B 5/6814* (2013.01)

(58) Field of Classification Search
None
See application file for complete search history.

(56) References Cited

U.S. PATENT DOCUMENTS

| 5,513,649 | A | 5/1996 | Gevins et al. |
| 7,286,871 | B2 | 10/2007 | Cohen |
| 8,538,512 | B1 | 9/2013 | Bibian et al. |
| 2005/0288954 | A1 | 12/2005 | McCarthy |
| 2007/0167858 | A1 | 7/2007 | Virtanen et al. |
| 2016/0157779 | A1 | 6/2016 | Baxi et al. |

FOREIGN PATENT DOCUMENTS

| WO | 2004000115 A1 | 12/2003 |
| WO | 2011149752 A1 | 12/2011 |
| WO | 2016026907 A2 | 2/2016 |

OTHER PUBLICATIONS

Salvo, et al., "A Wearable Sensor for Measuring Sweat Rate," IEEE Sensors Journal, vol. 10, No. 10 (Oct. 2010), pp. 1557-1558.

*Primary Examiner* — Eric F Winakur
*Assistant Examiner* — Marjan Fardanesh
(74) *Attorney, Agent, or Firm* — Intelletek Law Group, PLLC; Gabriel Daniel, Esq.

(57) ABSTRACT

A method and system of removing artifacts in electroencephalogram (EEG) signals is provided. Digital EEG data, based on a digitizing of analog EEG signals of a patient from a first electrode, is received. Digital sweat sensor data, based on a digitizing of analog sweat sensor signals of the patient that are contemporaneous with the analog EEG signals, is received. A transform is applied to the digital sweat sensor data based on a predetermined sweat stress profile of the patient. The digital EEG data is adaptively adjusted by subtracting the transformed sweat sensor data from the digital EEG data.

20 Claims, 8 Drawing Sheets

ADAPTIVE FILTRATION OF SWEAT ARTIFACTS DURING ELECTRONIC BRAIN MONITORING

BACKGROUND

Technical Field

The present disclosure generally relates to signal processing, and more particularly, to detection, identification, and removal of artifacts in neurophysiological signals.

Description of the Related Art

In recent years, brain computer interface and intelligent signal segmentation have attracted increasing interest in medicine. The brain electrical activity is represented by the electroencephalogram (EEG) signals. EEG is a test that detects electrical activity in a brain using electrodes (that may be in the form of small, flat metal discs) that are attached to a scalp. The brain cells communicate via electrical impulses and are active all the time, even when one is asleep. Such activity shows up as voltage fluctuations resulting from ionic current within the neurons of the brain.

As used herein, EEG refers to the recording of the brain's spontaneous electrical activity over a time period, as recorded from multiple electrodes placed on the scalp. Diagnostic applications generally focus on the spectral content of EEG, that is, the type of neural oscillations (sometimes referred to as "brain waves") that can be observed in EEG signals. An EEG is one of the main diagnostic tests for epilepsy and may also play a role in diagnosing other brain and sleep disorders. In order to increase the accuracy of the EEG measurements, electrical contaminants that may arise during the measurements that distort or drown out the true brain wave signals, referred to herein as artifacts, should be removed.

SUMMARY

According to various embodiments, a computing device, a non-transitory computer readable storage medium, and a method of removing artifacts in electroencephalogram (EEG) signals is provided. Analog EEG signals of a patient are received from a first electrode and converted to digital EEG data. Analog sweat sensor signals of the patient, which are contemporaneous with the analog EEG signals, are received and converted to digital sweat sensor data. A transform is applied to the digital sweat sensor data based on a predetermined sweat stress profile of the patient. The digital EEG data is adaptively adjusted by subtracting the transformed sweat sensor data from the digital EEG data. The adjusted digital EEG data is sent to be displayed on a user interface of the computer device.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

DETAILED DESCRIPTION

Overview

In the following detailed description, numerous specific details are set forth by way of examples to provide a thorough understanding of the relevant teachings. However, it should be apparent that the present teachings may be practiced without such details. In other instances, well-known methods, procedures, components, and/or circuitry have been described at a relatively high-level, without detail, to avoid unnecessarily obscuring aspects of the present teachings.

The present disclosure relates to detection, identification, and removal of artifacts in neurophysiological signals. Today, known available methods of automated EEG analysis for brain activity detection have a number of challenges that limit their dependability. Such drawbacks include biological artifacts and susceptibility to environmental noise/interference resulting in reduced reliability. As used herein the term "artefact" denotes all non-event signals that contaminate the event signal of interest.

One potential source of artifacts is sweat by the patient. Applicants have identified that sweat introduces a low-frequency interference source that hampers the analysis of an EEG signal measured, for example, from the forehead of the patient. While abrading the skin can reduce the effects of skin potentials to reduce the negative effects discussed herein, it is time consuming, potentially harmful, and may not be an option. For example, the EEG may be performed under sleep conditions or the patient may simply not be able to abrade the skin regularly during an EEG analysis.

The concepts discussed herein provide an automatic and efficient way of detecting and removing artifacts related to sweat that corrupt EEG signals in real-time, thereby providing a more accurate cognitive state assessment of a patient. To that end a computing device, which may be user device or a central server cooperating with a user device, receives analog EEG signals of a patient from a first electrode and converts the EEG signals to digital EEG data. Analog sweat sensor signals of the patient that are contemporaneous with the analog EEG signals are received and converted to digital sweat sensor data. A transform is applied to the digital sweat sensor data based on a predetermined sweat stress profile of the patient. The digital EEG data is then adaptively adjusted by subtracting the transformed sweat sensor data from the digital EEG data. The adjusted EEG data can then be sent to a user interface of the computing device in real time. Reference now is made in detail to the examples illustrated in the accompanying drawings and discussed below.

Example Architecture

Figure 1:
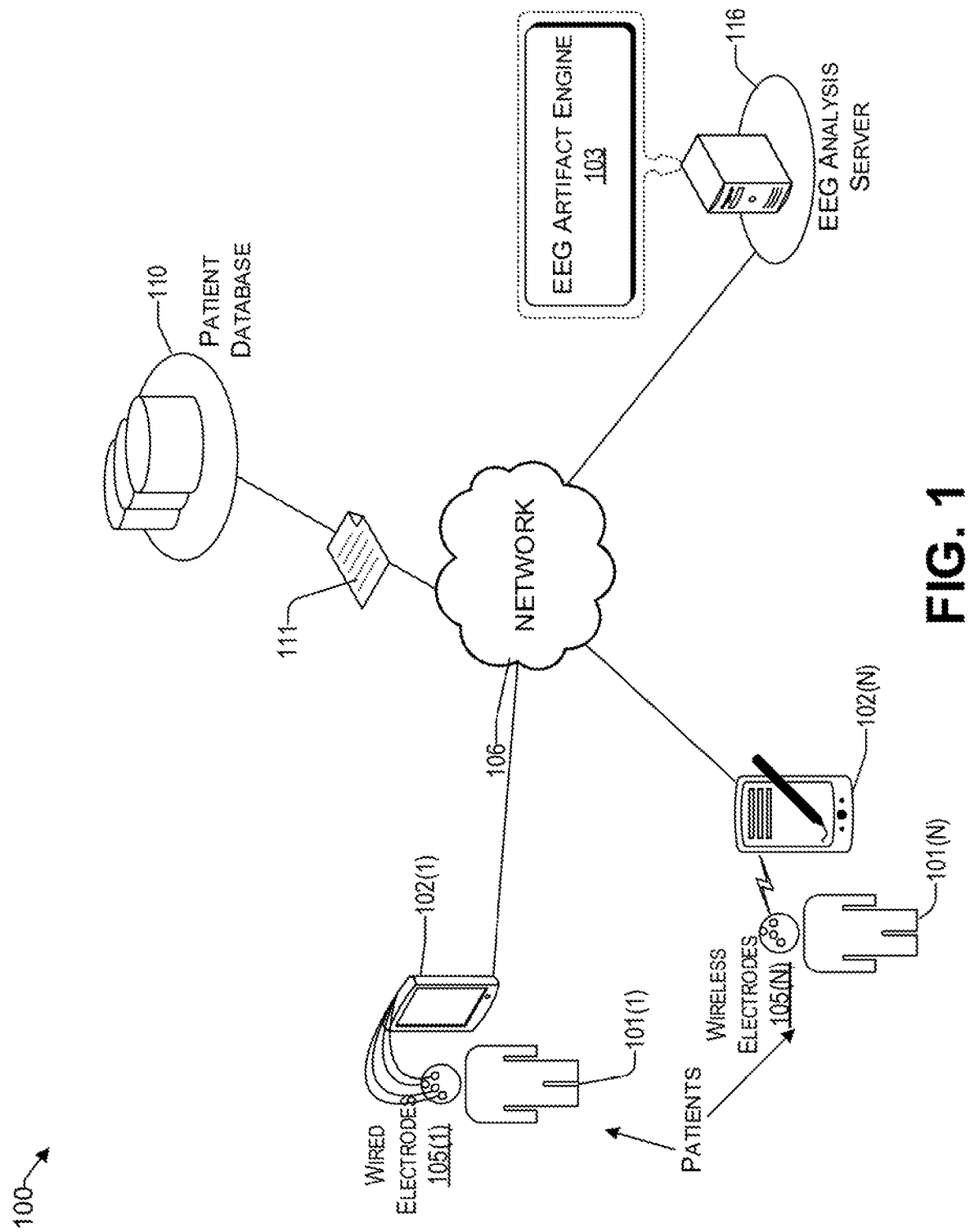
FIG. 1 illustrates an example architecture for implementing a system to perform adaptive filtration of sweat artifacts during electronic brain monitoring.

FIG. 1 illustrates an example architecture 100 for implementing a system to perform adaptive filtration of sweat artifacts during electronic brain monitoring. Architecture 100 may include a network 106 that allows patients 101(1) to 101(N) to communicate with various resources via their corresponding user device 102(1) to 102(N). Networked resources may include a patient database 110, an EEG analysis server 116 having an EEG artifact engine 103 running thereon, as well as any other components that are connected to the network 106.

The network 106 may be, without limitation, a local area network ("LAN"), a virtual private network ("VPN"), a cellular network, the Internet, or a combination thereof. For example, the network 106 may include a mobile network that is communicatively coupled to a private network, sometimes referred to as an intranet that provides various ancillary services, such as communication with a patient database 110, libraries, and the Internet. To facilitate the present discussion, network 106 will be described, by way of example only and not by way of limitation, as a mobile network as may be operated by a carrier or service provider to provide a wide range of mobile communication services and supplemental services or features to its subscriber customers and associated mobile device users. The network 106 allows data harvested from patients 101(1) to 101(N) to be communicated to the EEG artifact engine 103 on the EEG analysis server 116, as well as being recorded in the patient database 110.

For purposes of later discussion, several user devices appear in the drawing, to represent some examples of the devices that can harvest neurophysiological and/or sweat information from a patient via electrodes 105(1) to 105(N), and to receive various services via the network 106. Today, user devices typically take the form of portable handsets, smart-phones, tablet computers, personal digital assistants (PDAs), and smart watches, although they may be implemented in other form factors, including consumer, and medical electronic devices.

In one embodiment, the electrodes 105(1) and 105(N) are removably connected to the scalp of the patient 101(1) and 101(N), respectively. Different technologies may be used for the electrodes, which are divided herein in two groups: (i) electrophysiological signal electrodes and (ii) sweat monitor electrodes, collectively referred to herein as electrodes. In some embodiments, an electrode is configured to sense both electrophysiological signals as well as monitor sweat parameters. Put differently, a single electrode channel is operative to provide both EEG data and sweat data.

Regarding the former, an electrode is configured to collect brain activity or related data such as EEG data from the patient. In various embodiments, such electrodes may include surface or intracranial electrodes for measuring electrophysiological signals and brain related signals such as EEG, ECoG, EOG, EMG, and the like. In one embodiment, the sensors can also be magnetic electrodes that are configured to sense magnetic fields to acquire brain wave signals similar to those that can be obtained through, for example, an electrode applied to the patient's scalp.

For example, EEG electrodes, are placed on different locations on a patient's scalp to measure the neurophysiological signals of the patient. There may be several such electrodes, each providing a different channel of information to the user devices (e.g., 102(1) and 102(N)) coupled thereto. There are also sweat electrodes operative to measure an amount of sweat in the proximity of a corresponding EEG electrode.

In various embodiments, depending on the desired accuracy of the EEG data filtration discussed herein, the ratio of sweat electrode to the number of EEG electrodes may vary. For example, the ratio of sweat to EEG electrode may be 1:1; 1 to many (where the EEG electrodes are within a predetermined radius of a sweat electrode); or each EEG electrode may have embedded therein a sweat sensor. Put differently, the same electrode provides both sweat information and neurophysiological signals of the patient. Since sensitivity is inversely proportional to the distance between the EEG electrode and the sweat electrode, a compromise can be made to have good sensitivity and a difference in the sweat values greater than inaccuracy in the single sweat measurements. In one embodiment, a distance-regression calculation is performed to adjust the filtration (e.g., transform) based on the distance between the EEG electrode and the sweat sensor electrode.

In various embodiments, the electrodes (e.g., the sweat and/or the EEG) may be coupled to its corresponding user device via physical lines (e.g., cable wires) and/or wirelessly via short range wireless communication. For example, the wired communication between the electrodes of the patient 101(1) may be via separate wires via a harness of wires (e.g., in the form of a strip of wires) that is physically coupled to the user device 102(1).

In other embodiments, the communication between the electrodes 105(N) and user device 102(N) is performed via a short range wireless communication technology. The various short range wireless technologies to communicate with the user device 102(N) include, but are not limited to, Digital Enhanced Cordless Telecommunications (DECT), Near Field Communication (NFC), ZigBee, and Bluetooth. DECT technology (traditionally used for wireless home phone systems) uses substantially less energy than cellular systems. NFC is a set of standards for smart-phones and similar devices to establish radio communication with each other by touching them together or bringing them into close proximity, usually no more than a few centimeters. Since the range is small, there are substantial power consumption benefits. Bluetooth, while operating at longer distances than NFC, still saves a substantial amount of power compared to cellular systems. ZigBee is a low-cost, low-power, wireless mesh network standard. The mesh networking of ZigBee provides high reliability and more extensive range. Thus, the user device 102(N) can save power from a longer distance. Generally, low power-usage allows longer life and smaller batteries, providing for more ergonomic form factors of the user device 102(N) and or electrodes 105(N). For example, the electrodes can be part of a helmet that can be easily worn on the head of a patient. The wireless technology discussed herein provides for more comfort and mobility of the patient, while avoiding accidental severing of an electrode from being tethered to a receiver.

Figure 2:
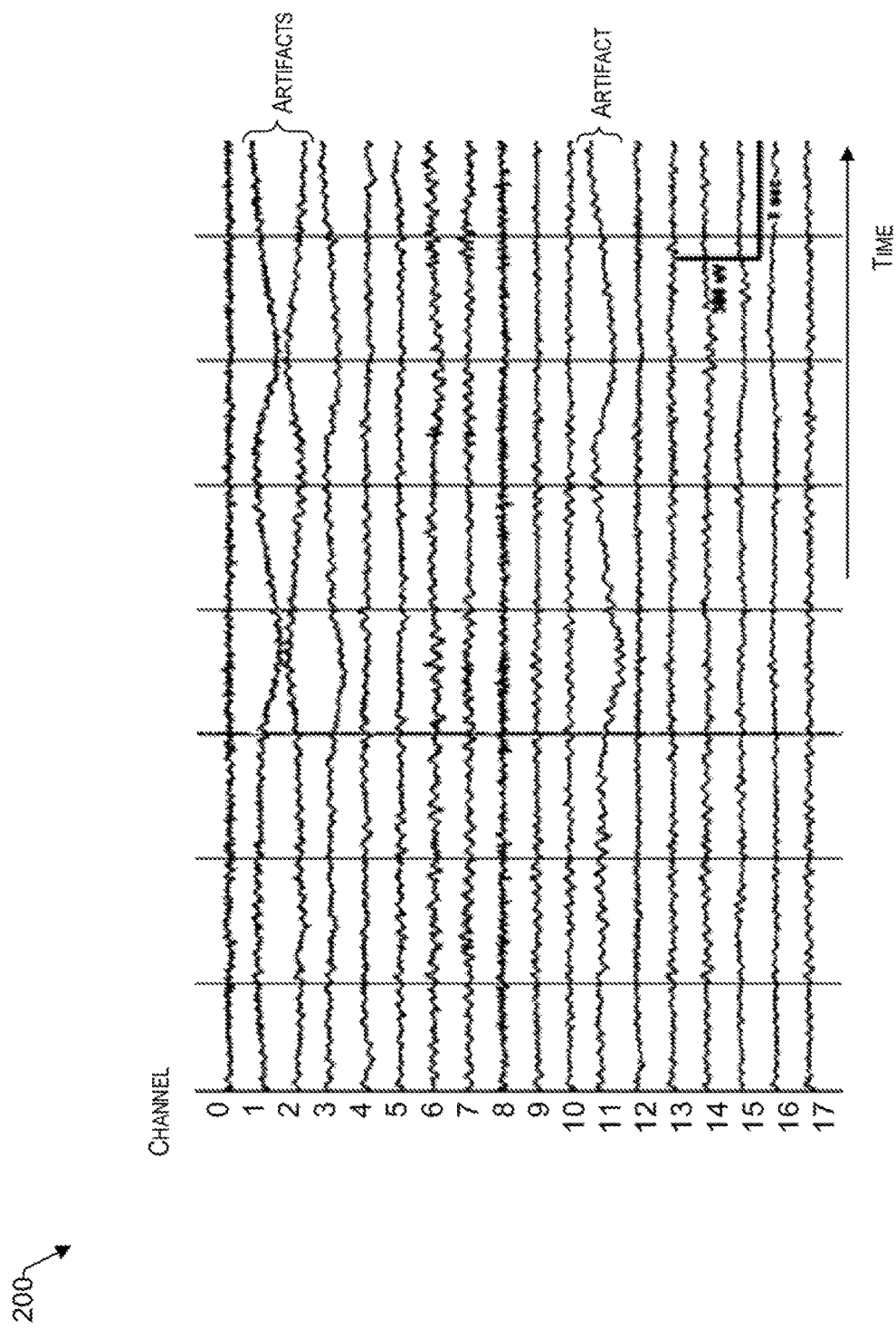
FIG. 2 illustrates signals of several EEG channels over time, consistent with an illustrative embodiment.

Applicants have identified that sweat introduces a low-frequency, large amplitude, interference source that hampers the analysis of an EEG signal measured, for example, from the forehead of the patient (e.g., 101(1)). In this regard, FIG. 2 illustrates signals of several EEG channels over time. Those familiar with EEG signal data understand that that such data has a "signature" where signals have a predetermined range in frequency and amplitude. An artifact in the form of sweat produces low-frequency, large amplitude shifts in EEG data, as demonstrated by the data of channels 1, 2, and 11. Accordingly, different locations on the body produce different results in a contemporaneous EEG measurement.

Referring back to FIG. 1, each user device (e.g., 102(1)) is configured to receive the electronic information harvested from the corresponding patient (either directly via a wire or wirelessly) and process the received information. For example, the user device 102(1) may receive EEG signals and sweat sensor signals of a patient 101(1) from one or more of the electrodes 105(1). The EEG signals and the sweat sensor signals are contemporaneous (e.g., are synchronous to each other). Initially, the harvested data is in analog form. Accordingly, the user device 102(1) converts the analog EEG signals and the analog sweat sensor signals into corresponding digital data. In various embodiments, this data can then be (i) further processed by the user device 102(1), or (ii) sent to the EEG analysis server 116 over the network 106 for further processing by the EEG artifact engine 103.

For example, the EEG artifact engine 103 may cooperate with a user device (e.g., 102(1) or 102(N)) to process the digital EEG data and the sweat data in real time to provide an adjusted digital EEG data that has removed therefrom the artifacts related to the perspiration of the patient. To that end, the EEG artifact engine 103 may receive a sweat stress profile 111 from a patient database 110.

The patient database 110 is coupled for communication via the network 106. In one embodiment, the patient database 110 provides on-line access to a variety of functions related to a patient's account, such as health data, sweat stress profile 111, subscription information, password control, etc.

Figure 3:
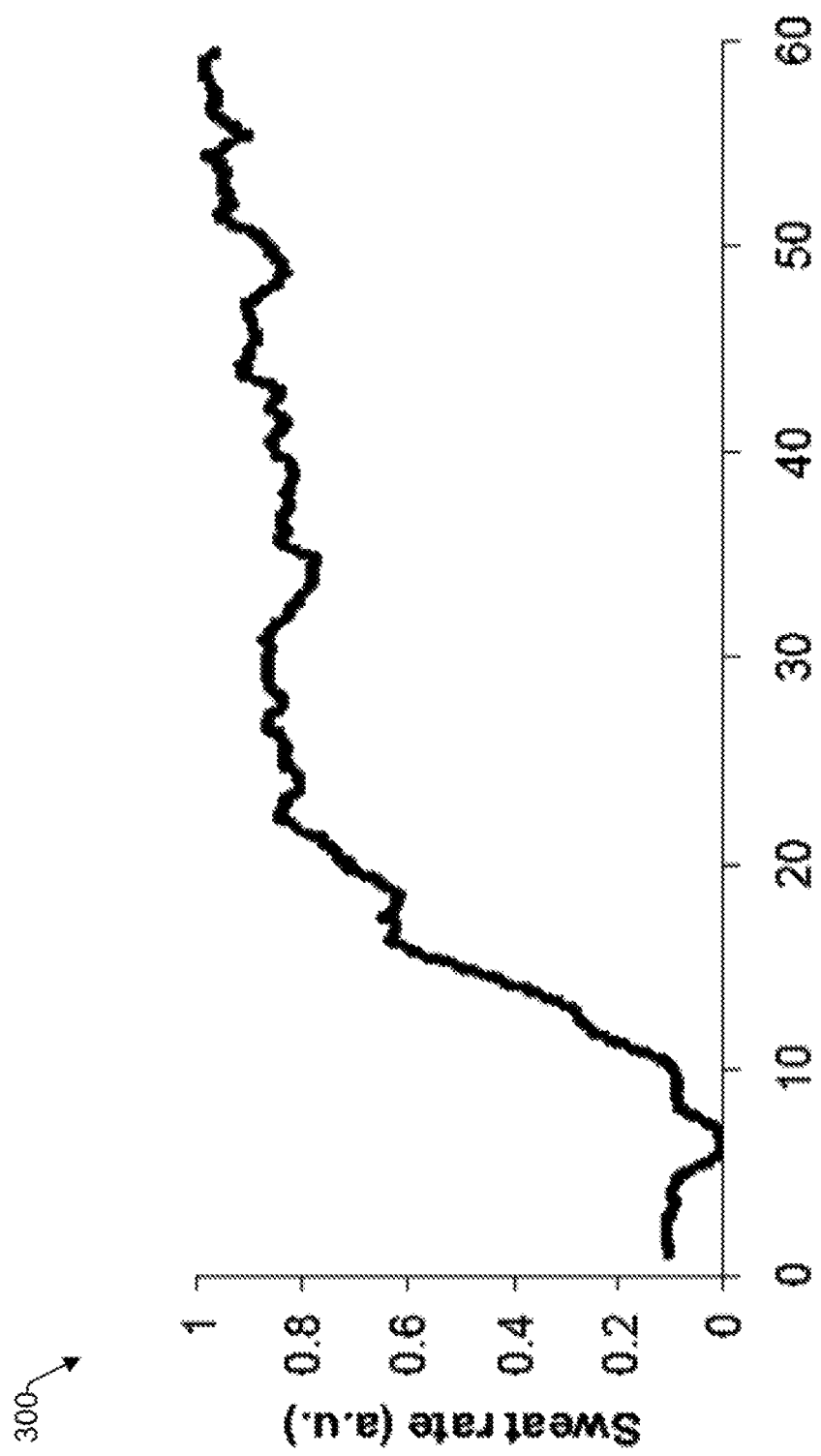
FIG. 3 is an example graph of sweat over time in response to various stressors for a patient, consistent with an illustrative embodiment.

In one embodiment, the sweat stress profile 111 stored in the patient database 110, may be generated during a training phase, where a sweat stress profile is created for a patient individually. In this regard, the patient's (e.g., 101(1)) reaction to controlled stressors is identified. For example, a patient may wear a virtual reality (VR) or an augmented reality (AR) interface to accelerate the physical exertion and reaction to audio, visual, and physical stressors. During the training phase, the sweat stress profile is identified over time in this controlled environment. FIG. 3 is an example graph 300 of sweat over time in response to various stressors, for a patient, consistent with an illustrative embodiment. In some embodiments, an EEG is performed during this phase to calibrate the filters for the patient individually.

For example, a patient may perform a motor task while wearing a VR headband that is integrated with EEG. The patient also wears a sweat sensor. At time 10, the sweat level increases beyond a pre-determined threshold, which is due to controlled changes in the physiological environment (e.g., temperature increase, movement, etc.). At that time, the filter is turned ON and is adaptively modified to reduce the error between the generated output and real output using an iterative procedure.

During the training phase, it is determined what the electrodermal sensitivity of the patient is (e.g., how sweat affects the neurophysiological signal levels). Some patients may be strongly affected (e.g., their cranial width may be relatively thin or the amplitude of their neural signals may be relatively low, which may affect the measured signal levels differently from those who have a thicker cranial width and/or who have higher amplitudes in their observed neurophysiological signals. Further, some patients may have different personalities and different levels of anxiety during testing. In this regard, in one embodiment, a baseline is determined for each patient, sometimes referred to herein as the sweat stress profile, which is stored in the patient database 110. In this way, a computing device can determine how a particular patient's EEG response is affected by their sweat production.

In one embodiment, the appropriate filter to be used for the digital EEG data is determined during the training phase. For example, different types of filters, including, but not limited to, least mean square (LMS), recursive least squares (RLS), Kalman, etc., may be evaluated to determine the one or more that best fit the physiological response of the patient to sweat. In this regard, it is noted that RLS algorithms may be faster to converge than LMS, but also are typically more complex. If the sweat artifact is limited to a narrowband signal, then an LMS algorithm may provide superior performance in terms of accuracy. Kalman filters may be more complex than RLS algorithms, but also show higher performance, as they do not require stationarity, and thus may be implemented if the artifacts to be removed are highly variable in time. Finally, if the artifact signal is determined to be non-linear, then a nonlinear filter (particle filter, batch filter, denoising or stacked autoencoders, etc.) may be used. Deep neural network-based models may be used, once a sufficient amount of training data is generated.

Referring back to FIG. 1, while the functionality of the EEG artifact engine 103 has been discussed in the context of an EEG analysis server 116, in one embodiment, some or all of the functions of the EEG artifact engine 103 may be included in the user device (e.g., 102(1) or 102(N)) itself. Stated differently, a user device may provide the functions of adaptive filtration of sweat artifacts during electronic brain monitoring, independent of the EEG analysis server 116.

While the patient database 110, the computing device (e.g., 102(1)), and the EEG analysis server 116 are illustrated by way of example to be on different platforms, it will be understood that in various embodiments, the patient database 110, EEG analysis server 116, and the user device (e.g., 102(1)) may be combined in various combinations. In other embodiments, these computing platforms may be implemented by virtual computing devices in the form of virtual machines or software containers that are hosted in a cloud, thereby providing an elastic architecture for processing and storage.

Each of the databases and computing devices discussed herein are compliant with the Health Insurance Portability and Accountability Act (HIPAA), which sets the standard for protecting sensitive patient data.

Example User Device

Figure 4:
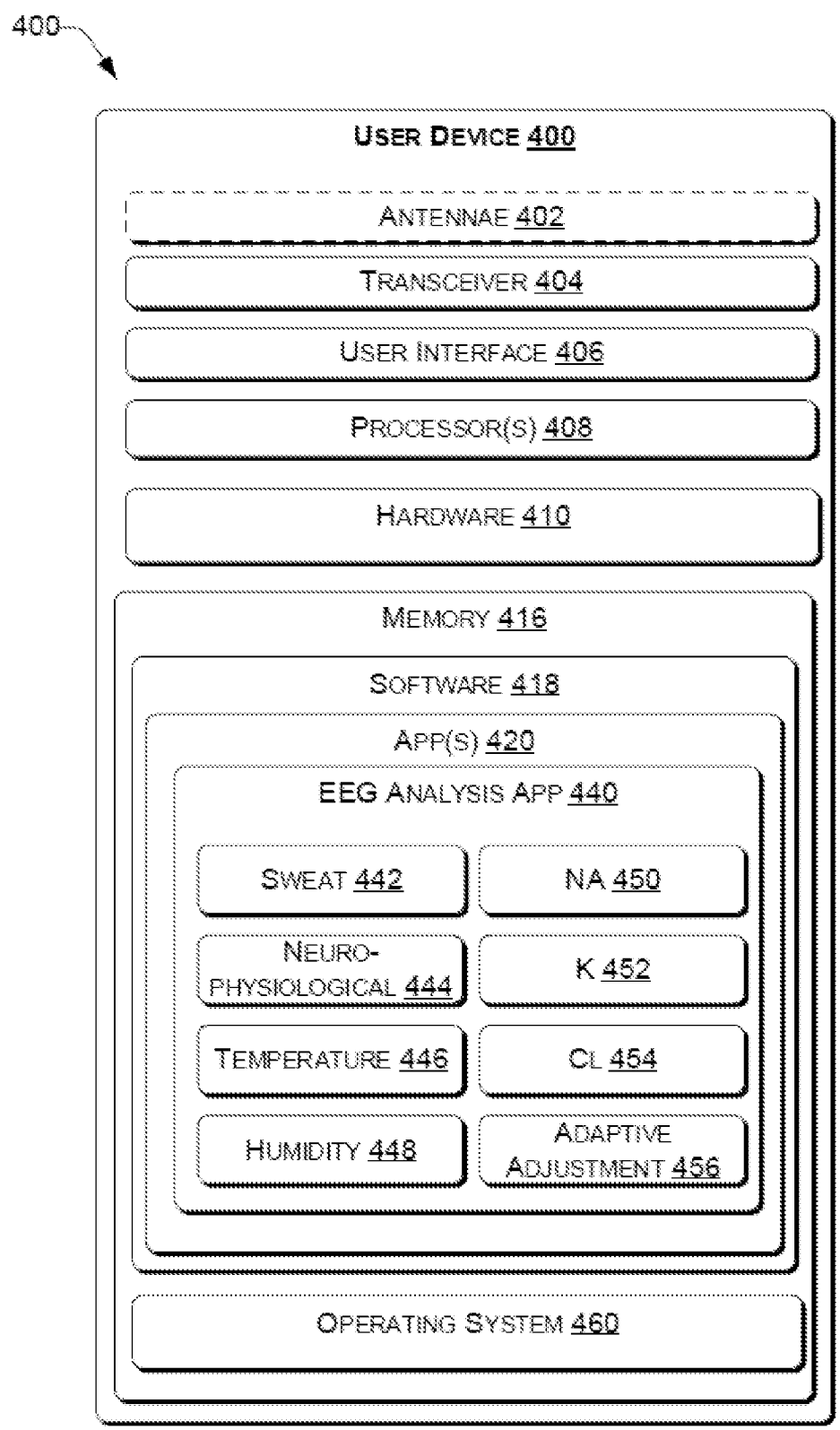
FIG. 4 illustrates a block diagram showing various components of an illustrative user device at a high level.

As discussed in the context of FIG. 1, the adaptive filtration of sweat artifacts during electronic brain monitoring system in the architecture 100 may involve different types of user devices. To that end, FIG. 4 illustrates a block diagram showing various components of an illustrative user device 400 at a high level. For discussion purposes, the illustration shows the user device 400 in the form of a wireless computing device that can communicate over the network 106 of FIG. 1.

The user device 400 may include one or more antennae 402; a transceiver 404 for cellular, Wi-Fi communication, and/or wired communication; a user interface 406; one or more processors 408; hardware 410; and memory 416. In some embodiments, the antennae 402 may include an uplink antenna that sends radio signals to a base station, and a downlink antenna that receives radio signals from the base station. In some other embodiments, a single antenna may both send and receive radio signals. The same or other antennas may be used for Wi-Fi communication. These signals may be processed by the transceiver 404, sometimes collectively referred to as a network interface, which is configured to receive and transmit digital data. In one embodiment, the transceiver 404 additionally includes short range wireless communication capability, such as DECT, NFC, ZigBee, Bluetooth, etc. In one embodiment, the user device 400 does not include an antenna 402 and communication with external components is via wired communication.

In one embodiment, the user device 400 includes a user interface 406 that enables a user to provide input and receive output from the user device 400. For example, the user interface 406 may include a data output device (e.g., visual display, audio speakers, haptic device, etc.) that may be used to provide notifications from the EEG artifact engine 103 of the EEG analysis server 116.

The user interface 406 may also include one or more data input devices. The data input devices may include, but are not limited to, combinations of one or more of keypads, keyboards, mouse devices, touch screens, microphones, speech recognition packages, and any other suitable devices or other electronic/software selection interfaces. Data input devices may also include ports, such as USB, that are configured to couple with the wired electrodes discussed herein.

The user device 400 may include one or more processors 408, which may be a single-core processor, a multi-core processor, a complex instruction set computing (CISC) processor, or another type of processor.

The hardware 410 may include a power source and digital signal processors (DSPs), which may include single-core or multiple-core processors. The hardware 410 may also include network processors that manage high-speed communication interfaces, including communication interfaces that interact with peripheral components. The network processors and the peripheral components may be linked by switching fabric. The hardware 410 may further include hardware decoders and encoders, analog to digital converters (ADC's), a network interface controller, and/or a USB controller. Still further, the hardware may include a temperature sensor, a humidity sensor, accelerometer, and a global positioning system (GPS). For example, the temperature and humidity sensors may be used to determine the ambient temperature and humidity of the environment that the patient is in. Further the accelerometer and GPS may be used to determine the position of the patient and whether the patient is moving.

The memory 416 may be implemented using computer-readable media, such as computer storage media. Storage media includes volatile and non-volatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD), high definition video storage disks, or other optical storage, magnetic cassettes, magnetic tape, magnetic disk storage or other magnetic storage devices, or any other non-transmission medium that can be used to store information for access by a computing device.

The memory 416 may store various software components or modules that are executable or accessible by the processor(s) 408 and controller(s) of the user device 400. The various components of the memory 416 may include software 418 and an operating system 450. The software 418 may include various applications 420, such as an EEG Analysis App 440 having several modules. Each module may include routines, program instructions, objects, and/or data structures that perform tasks or implement abstract data types.

For example, the EEG Analysis App 440 of the user device 400 may include a sweat module 442 operative to interpret the wearable digital sweat sensor data. In one embodiment, a wearable sweat sensor mainly measures galvanic skin response (GSR), which may be performed by placing two electrodes a predetermined distance (e.g., an inch) apart on the body and/or scalp surface and measuring recorded electrical resistance between the two electrodes when a very weak current is steadily passed between them. Galvanic skin potential (GSP) can be measured between two electrodes without any externally applied current, when the electrodes are connected to a voltage amplifier. Both GSR and GSP vary with the emotional state of the subject (e.g., arousal) as well as with the body temperature and humidity. The wearable sweat sensor can be integrated in the EEG headband or can be worn at any other part of the body.

There may be a neurophysiological module 444 operative to interpret the digital EEG data. There may be a temperature module 446 operative to interpret the ambient temperature conditions provided by a temperature sensor. There may be a humidity module 448 operative to determine the humidity of the environment the patient is in. There may also be NA 450, K 452, and Cl 454 modules that are operative to determine the biomarkers present in sweat, such as sodium (NA+), potassium (K+), chloride (Cl−), glucose, lactose, etc., content, respectively, of the digital sweat sensor data. A combination of the biomarker content with GSR signal can be used to separate the emotional and cognitive components from the physiological component present in sweat secretion, which can then be used to correct the EEG signal.

In a special embodiment, the EEG Analysis App 440 includes an adaptive adjustment module 456 that is operative to apply a transform to the sweat sensor data based on a predetermined sweat stress profile of the patient. The EEG Analysis App 440 then adaptively subtract the transformed sweat sensor data from the digital EEG data.

While a EEG Analysis App 440 has been illustrated to be part of the user device 400, in some embodiments, the functions performed by the EEG Analysis App 440, may be performed by the EEG Artifact Engine 103. For example, the functions associated with the adaptive adjustment module 456 may be performed by the EEG Artifact Engine 103 of the EEG Analysis server 116. The operation of the EEG Analysis server 116 is discussed in more detail later.

The operating system 450 may include components that enable the user device 400 to receive and transmit data via various interfaces (e.g., user controls, communication interface, and/or memory input/output devices), as well as process data using the processor(s) 408 to generate output. The operating system 450 may include a presentation component that presents the output (e.g., display the data on an electronic display of the user device 400, store the data in memory 416, transmit the data to another electronic device, etc.). Additionally, the operating system 450 may include other components that perform various additional functions generally associated with an operating system 450.

Example Block Diagram

Figure 5:
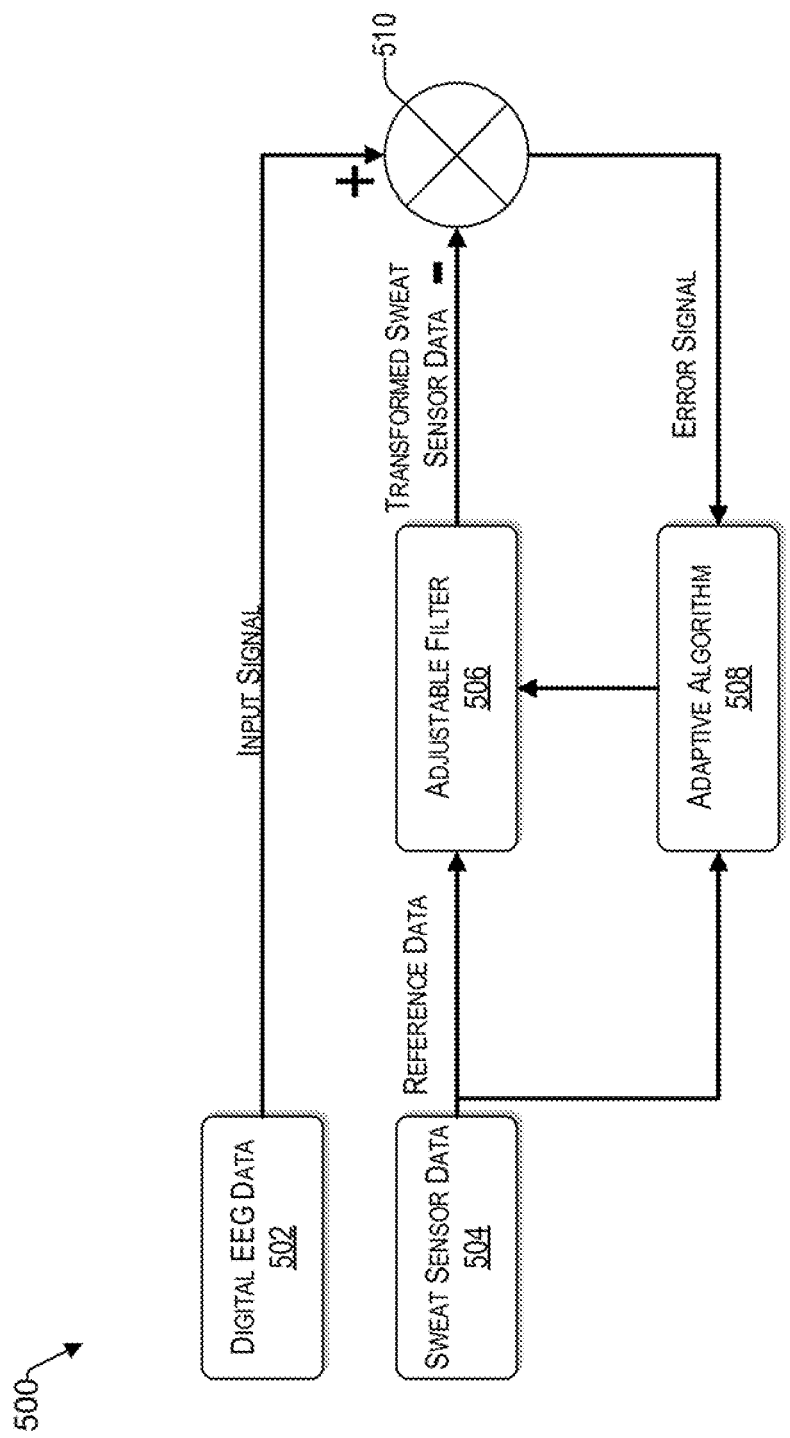
FIG. 5 illustrates a high-level block diagram of an adaptive filtration of sweat artifacts system, consistent with an illustrative embodiment.

FIG. 5 illustrates a high-level block diagram of an adaptive filtration of sweat artifacts system 500, consistent with an illustrative embodiment. The system 500 includes a summing node 510, which may represent the EEG Analysis App 440 of a user device 400 or an EEG Artifact Engine 103. The EEG signals of a patient are received from various electrodes. Block 502 represents a single channel that has been digitized. The sweat sensor signals of the patient are received contemporaneously. Block 504 represents the digitized sweat sensor data. The adjustable filter 506, sometimes referred to herein as a transform, receives the sweat sensor data 504 and adaptively adjusts the sweat sensor data based on the control signal received by the adaptive algorithm 508. The adaptive algorithm 508 is configured during a training phase, where the sweat stress profile is determined. The sweat stress profile of the patient is used to create the adaptive algorithm to adjust the filter 506. Accordingly, the adjustable filter 506 generates a digital signal level for each sample of the digital EEG data. For each sample of the digital EEG data, the summing node 510 subtracts the transformed sweat sensor data therefrom.

In one embodiment, the coefficients and/or the hyperparameters of the adjustable filter 506 are determined during the training, where the desired output is pre-computed or is estimated from other environment variables and/or data from other sensors (e.g., temperature sensor, humidity sensor, etc.). The error function, sometimes referred to herein as the error signal, is estimated by the difference between the desired output and the actual output. The coefficients and/or hyperparameters are optimized such that the error function is minimized. The trained adaptive algorithm 508 is then used to remove the artifact from the test EEG signal. In some embodiments, the adjustable filter 506 is further adjusted based on the ambient conditions during the evaluation of the patient.

Example Process

Figure 6:
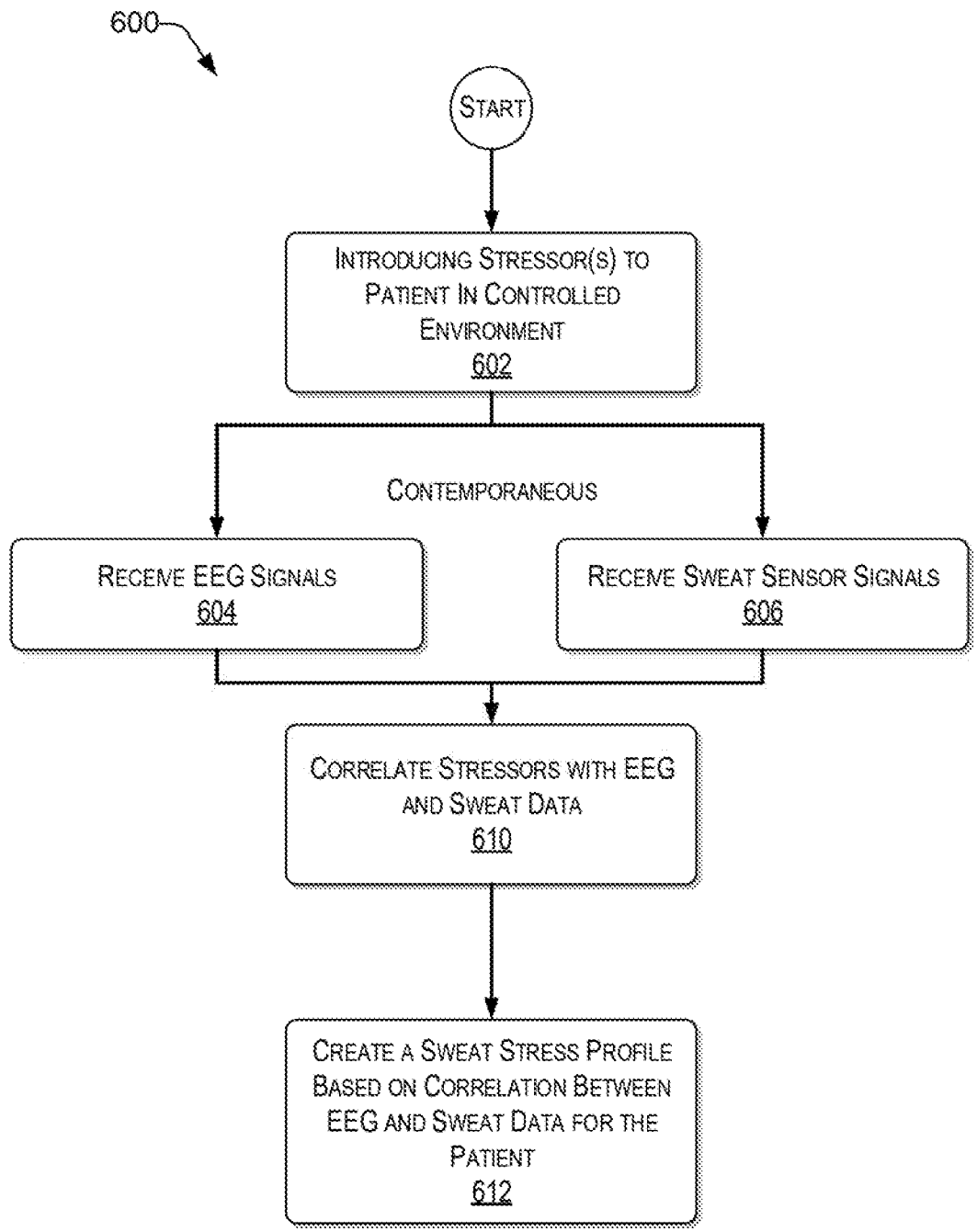
FIG. 6 illustrates an example process of an initialization training phase, where a sweat stress profile is tailored for an individual patient.
Figure 7:
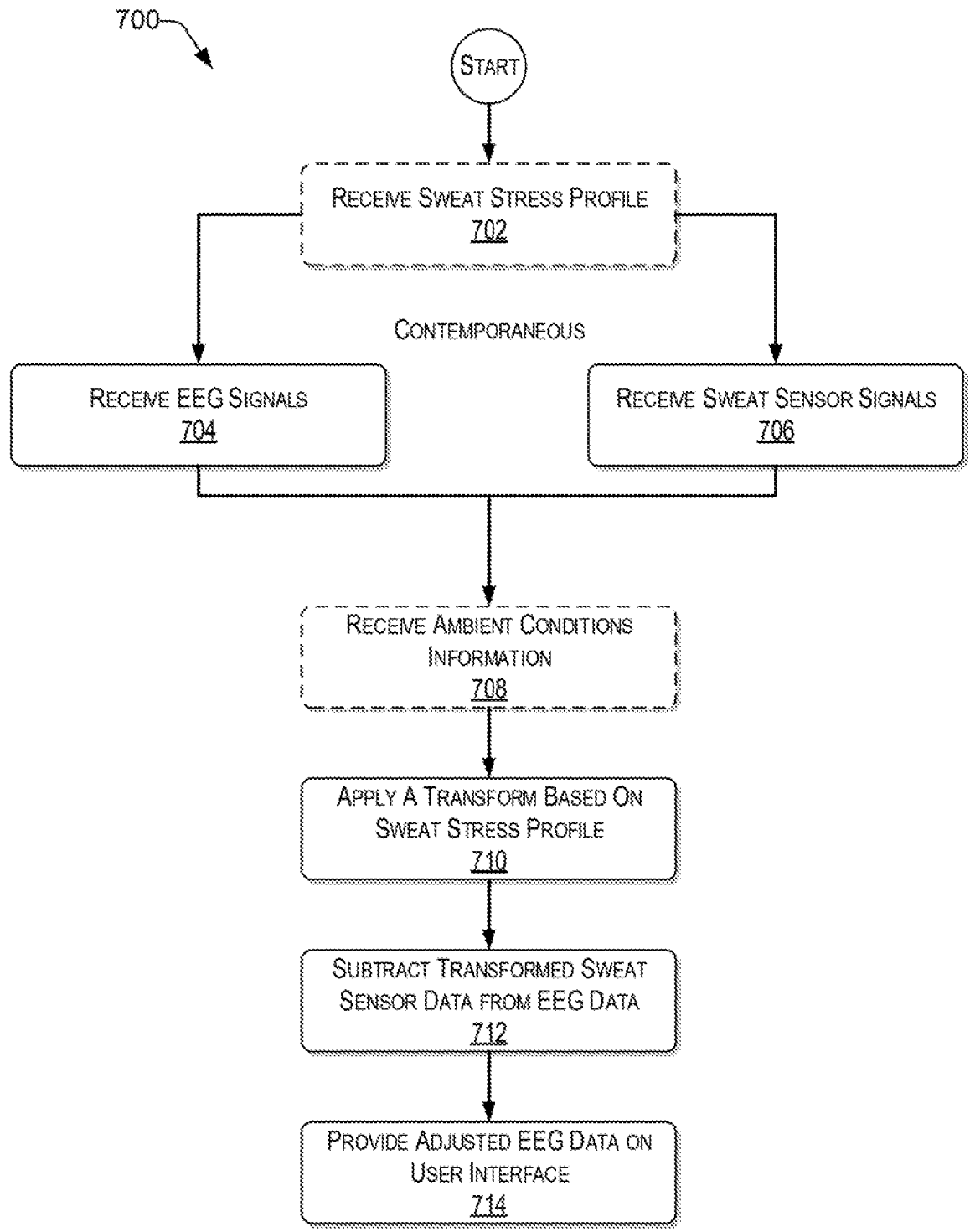
FIG. 7 illustrates an example process of an active phase where artifacts related to sweat are identified and removed from EEG data.

With the foregoing overview of the example architecture 100 and example block diagram 500, it may be helpful now to consider a high-level discussion of an example process. To that end, FIGS. 6 and 7 presents illustrative processes 600 and 700 for the detection, identification, and removal of artifacts in neurophysiological signals during electronic brain monitoring of a patient. More particularly, FIG. 6 illustrates an example process of an initialization training phase, where a sweat stress profile is tailored for an individual patient, and FIG. 7 illustrates an example process of an active phase where artifacts related to sweat are identified and removed from EEG data.

Processes 600 and 700 are illustrated as collections of blocks in logical flowcharts, which represent sequences of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform functions or implement abstract data types. The order in which the operations are described is not intended to be construed as a limitation, and any number of the described blocks can be combined in any order and/or performed in parallel to implement the process. For discussion purposes, the processes 600 and 700 are described with reference to the architecture 100 of FIG. 1.

At block 602, a patient is placed in a controlled environment to create a sweat stress profile that is particular to the patient. To that end, the controlled environment may include the patient wearing a VR or AR interface to accelerate the physical exertion and reaction to audio, video, and physical stressors. In some embodiments, the ambient temperature and/or the humidity of the room is controlled to identify how the patient reacts to the introduced stressors.

At block 604, analog EEG signals of the patient are received from one or more electrodes by a computing device. As discussed previously, in various embodiments, the computing device may be a user device, such as user device 102(1), or the EEG analysis server 116. These analog signals are converted into digital training EEG data.

At block 606, analog sweat sensor signals of the patient, which are contemporaneous with the analog EEG signals, are received by the computing device. For example, the sweat sensor signals are contemporaneous with the EEG signals in that the sweat sensor signals are synchronous with the EEG signals. These analog sweat sensor signals are converted to digital training sweat sensor data. In some embodiments, different time segments of this training phase expose the subject patient to different stressors. For example, during time segment 0<T<5 min, soothing music is played, serene scenes are displayed in the VR or AR interface, and comfortable ambient conditions are maintained; during time segment 5 min≤T<10 min the ambient conditions may be aggravated (e.g., higher temperature and/or humidity); during time segment 10 min≤T<15 min the VR or AR interface may display stressful scenes to accelerate the physical exertion and reaction to audio, visual, and physical stressors; etc.

At block 610, the digital training EEG data, digital training sweat sensor data, and the stressors are correlated.

At block 612, a sweat stress profile for the subject patient is created based on the correlation performed at block 610. In various embodiments, the sweat stress profile for the subject patient may be stored in the user device (e.g., 102(1)) and/or sent over the network 106 to be stored in the patient database 110.

Reference now is made to FIG. 7, which illustrates an example process 700 of an active phase, where artifacts related to sweat are identified and removed from EEG data by a computing device. The computing device may be a user device (e.g., 102(1)) or the EEG analysis server 116. In various embodiments, process 700 may be independent from process 600 or may be run thereafter (i.e., to use the sweat stress profile from process 600). Accordingly, at block 702 the sweat stress profile of the subject patient is received. In various embodiments, the sweat stress profile may be received over the network 106 from the patient database 110 or directly from the user device (e.g., 102(1)).

At block 704, analog EEG signals of the patient are received from one or more electrodes by a computing device, which, in various embodiments, may be a user device (e.g., 102(1)), or the EEG analysis server 116. These analog signals are converted into digital EEG data.

At block 706, analog sweat sensor signals of the patient, which are contemporaneous with the analog EEG signals, are received by the computing device. These analog sweat sensor signals are converted to digital sweat sensor data.

At block 708, in one embodiment, ambient conditions data are received by the computing device. For example, the ambient conditions data may include, without limitation, (i) the ambient temperature, (ii) the ambient humidity, (iii) an ambient airflow, etc., from one or more ambient sensors in the proximity of the subject patient.

At block 710, a transform is applied to the digital sweat sensor data. In one embodiment, the transform is based on the predetermined sweat stress profile that was received by the computing device (e.g., block 702). In some embodiments (e.g., where the ambient conditions were measured in block 708, the transform is further based on the ambient conditions. Accordingly, block 710 provides a transformed digital sweat sensor data that can be used as a filtration reference.

At block 712, the transformed digital sweat sensor data is subtracted from the digital EEG data, thereby removing the artifact related to sweat from the digital EEG data. Accordingly, the computing device adaptively adjusts the digital EEG data. Thus, for every sample, an appropriate amount is subtracted from the digital EEG data to remove the sweat artifacts therefrom.

At block 714, the adaptively adjusted digital EEG data is displayed on a user interface of the user device (e.g., 102(1)). The presentation of the adjusted digital EEG data can be performed in real time.

Example Computer Platform

Figure 8:
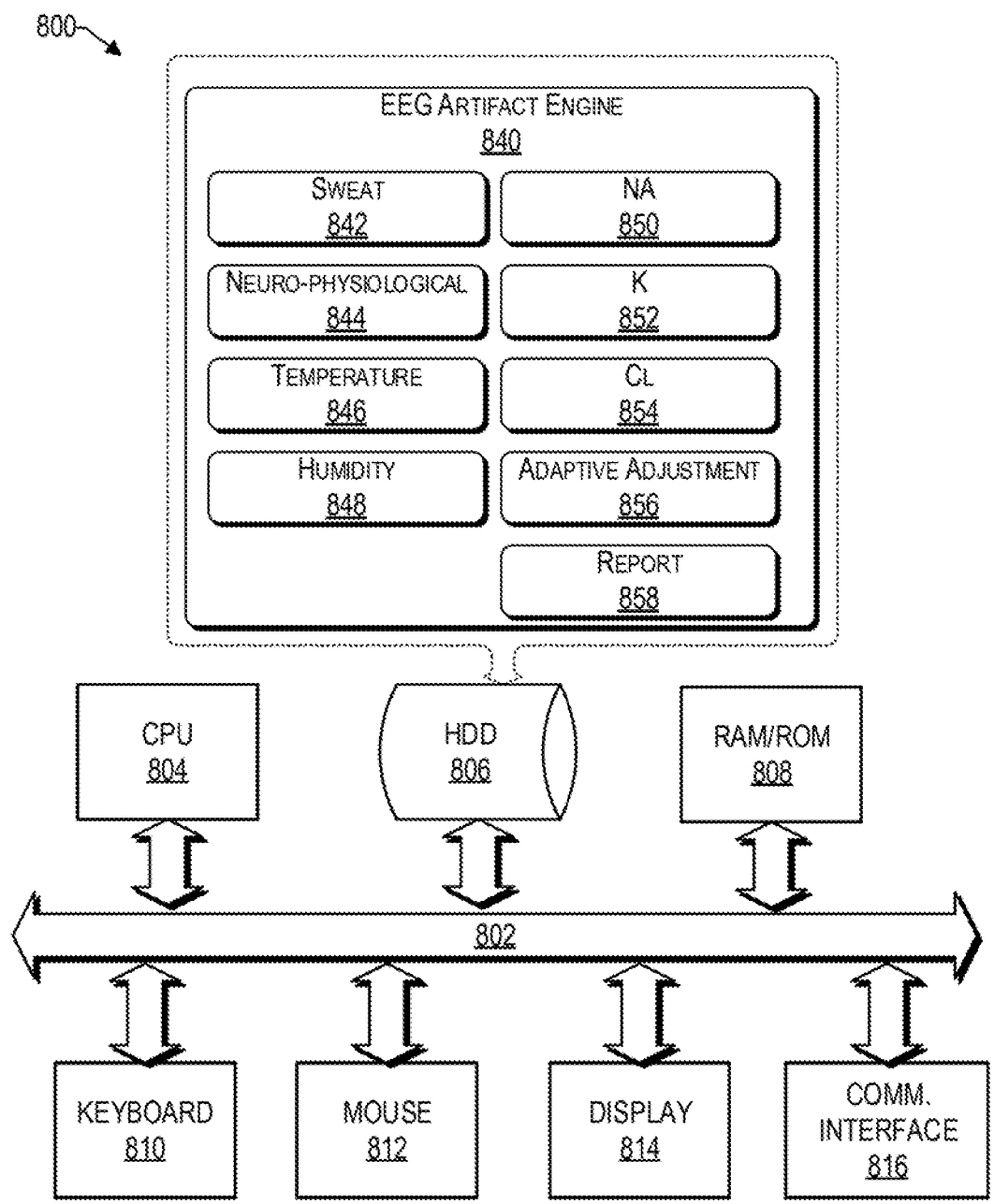
FIG. 8 is a functional block diagram illustration of a computer hardware platform that can communicate with various networked components, consistent with an illustrative embodiment.

As discussed above, functions relating to detection, identification, and removal of artifacts in neurophysiological signals can be performed with the use of one or more computing devices connected for data communication via wireless or wired communication, as shown in FIG. 1 and in accordance with the process 600 of FIG. 6 and 700 of FIG. 7, FIG. 8 is a functional block diagram illustration of a computer hardware platform that can communicate with various networked components, such as user devices 102(1) to 102(N) of patients, patient databases, such as patient database 110, etc. In particular, FIG. 8 illustrates a network or host computer platform 800, as may be used to implement a server, such as the EEG Analysis Server 116 of FIG. 1.

The computer platform 800 may include a central processing unit (CPU) 804, a hard disk drive (HDD) 806, random access memory (RAM) and/or read only memory (ROM) 808, a keyboard 810, a mouse 812, a display 814, and a communication interface 816, which are connected to a system bus 802.

In one embodiment, the HDD 806, has capabilities that include storing a program that can execute various processes, such as the EEG Artifact Engine 840, in a manner described herein. The EEG Artifact Engine 840 may have various modules configured to perform different functions. As mentioned in the context of the discussion of the user device 400 of FIG. 4, in various embodiments, some or all of the functions described below can be performed by the user device 400 itself. Stated differently, the EEG Analysis App 440 of the user device 400 can perform the functionality of the EEG Artifact Engine 840 discussed below.

For example, the EEG Artifact Engine 840 may include a sweat module 842 operative to interpret the digital sweat sensor data received from the user device (e.g., 102(1)). There may be a neurophysiological module 844 operative to interpret the digital EEG data received by the user device (e.g., 102(1)). There may be a temperature module 846 operative to interpret the ambient temperature conditions provided by a temperature sensor. There may be a humidity module 848 operative to determine the humidity of the environment the patient is in. There may also be NA 850, K 852, and Cl 854 modules that are operative to determine the NA+, K+, and Cl− content, respectively, of the digital sweat sensor data. There may be additional modules (not shown) to measure additional parameters, such as glucose, lactose, etc.

In one embodiment, there is a report module 858 operative to report the adaptively adjusted digital EEG data to an appropriate recipient, such as a responsible nurse, physician, or the patient itself. For example, the adaptively adjusted digital EEG data can be sent over the network 106 to a user device of a patient, such that is displayed on a user interface thereof. The reporting of the adjusted digital EEG data can be performed in real time In one embodiment, a program, such as Apache™, can be stored for operating the system as a Web server. In one embodiment, the HDD 806 can store an executing application that includes one or more library software modules, such as those for the Java™ Runtime Environment program for realizing a JVM (Java™ virtual machine).

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

Aspects of the present disclosure are described herein with reference to a flowchart illustration and/or block diagram of a method, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures herein illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A computing device comprising:
a processor;
a network interface coupled to the processor to enable communication over a network;
a storage device coupled to the processor;
a software stored in the storage device, wherein an execution of the software by the processor configures the computing device to perform acts comprising:
receiving digital EEG data based on a digitizing of analog electroencephalogram (EEG) signals of a patient from a first electrode;
receiving digital sweat sensor data based on a digitizing of analog sweat sensor signals of the patient that are contemporaneous with the analog EEG signals;
applying a transform to the digital sweat sensor data based on a predetermined sweat stress profile of the patient; and
adaptively adjusting the digital EEG data by subtracting the transformed sweat sensor data from the digital EEG data.

2. The computing device of claim 1, wherein the adaptive adjustment of the digital EEG data is in real time with the receipt of the analog EEG and sweat sensor signals.

3. The computing device of claim 1, wherein the sweat sensor data comprises a sodium (NA+) measurement data, a potassium (K+) measurement data, and a chlorine (Cl−) measurement data.

4. The computing device of claim 1, wherein the analog sweat sensor signals are based on a galvanic skin response by measuring an electrical resistance between the first electrode and a second electrode when a current is applied between the first electrode and the second electrode.

5. The computing device of claim 1, wherein:
the first electrode is part of a group of a plurality of electrodes configured to receive analog EEG signals from different parts of a scalp of the patient, and
analog sweat sensor signals are received from a sweat sensor electrode for one or more electrodes of the plurality of electrodes that are within a predetermined distance of the sweat sensor.

6. The computing device of claim 1, wherein execution of the software by the processor further configures the computing device to perform acts comprising: performing a distance-regression adjustment of the transform based on a distance between the first electrode and a sweat sensor electrode, before applying the transform to the digital sweat sensor data.

7. The computing device of claim 1, wherein execution of the software by the processor further configures the computing device to perform acts comprising: receiving ambient data of an environment of the patient, comprising at least one of: (i) an ambient temperature, (ii) an ambient humidity, (iii) and an ambient air-flow, from one or more ambient sensors, wherein applying a transform to the digital sweat sensor data is further based on the received ambient data.

8. The computing device of claim 1, wherein:
the sweat stress profile of the patient is predetermined during a training phase, and
execution of the software by the processor further configures the computing device to perform acts comprising:
introducing stressors to the patient in a controlled environment;
receiving training analog EEG signals of a patient from the first electrode in response to the stressors and converting the training analog EEG signals to training digital EEG data;
receiving training analog sweat sensor signals of the patient in response to the stressors that are contemporaneous with the training analog EEG signals and converting the training analog sweat sensor signals to digital sweat sensor data; and
creating a sweat stress profile of the patient based on the digital training EEG data and the digital training sweat sensor data.

9. The computing device of claim 8, wherein the stressors are introduced via at least one of: (i) a virtual reality (VR) interface of the computing device, (ii) an augmented reality (AR) interface of the computing device, (iii) a control of an ambient temperature of the controlled environment, (iv) a control of an ambient humidity of the controlled environment, and (v) a control of an ambient air-flow of the controlled environment.

10. The computing device of claim 1, wherein the analog EEG signals and the analog sweat sensor signals are received wirelessly and in real time by the computing device, via a short range wireless communication technology.

11. A non-transitory computer readable storage medium tangibly embodying a computer readable program code having computer readable instructions that, when executed, causes a computer device to carry out a method of removing artifacts in electroencephalogram (EEG) signals, the method comprising:
receiving digital EEG data based on a digitizing of analog EEG signals of a patient from a first electrode;
receiving digital sweat sensor data based on a digitizing of analog sweat sensor signals of the patient that are contemporaneous with the analog EEG signals;
applying a transform to the digital sweat sensor data based on a predetermined sweat stress profile of the patient; and
adaptively adjusting the digital EEG data by subtracting the transformed sweat sensor data from the digital EEG data.

12. The non-transitory computer readable storage medium of claim 11, wherein the adaptive adjustment of the digital EEG data is in real time with the receipt of the analog EEG and sweat sensor signals.

13. The non-transitory computer readable storage medium of claim 11, wherein the sweat sensor data comprises a sodium (NA+) measurement data, a potassium (K+) measurement data, and a chlorine (Cl-) measurement data.

14. The non-transitory computer readable storage medium of claim 11, wherein the analog sweat sensor signals are based on a galvanic skin response by measuring an electrical resistance between the first electrode and a second electrode when a current is applied between the first electrode and the second electrode.

15. The computing device of claim 1, wherein:
the first electrode is part of a group of a plurality of electrodes configured to receive analog EEG signals from different parts of a scalp of the patient, and
analog sweat sensor signals are received from a sweat sensor electrode for one or more electrodes of the plurality of electrodes that are within a predetermined distance of the sweat sensor.

16. The non-transitory computer readable storage medium of claim 11, further comprising, performing a distance-regression adjustment of the transform based on a distance between the first electrode and a sweat sensor electrode, before applying the transform to the digital sweat sensor data.

17. The non-transitory computer readable storage medium of claim 11, further comprising, receiving ambient data of an environment of the patient, comprising at least one of: (i) an ambient temperature, (ii) an ambient humidity, (iii) and an ambient air-flow, from one or more ambient sensors, wherein applying a transform to the digital sweat sensor data is further based on the received ambient data.

18. The non-transitory computer readable storage medium of claim 11, wherein determining the sweat stress profile comprises, during a training phase:
introducing stressors to the patient in a controlled environment;
receiving training analog EEG signals of a patient from the first electrode in response to the stressors and converting the training analog EEG signals to training digital EEG data;
receiving training analog sweat sensor signals of the patient in response to the stressors that are contemporaneous with the training analog EEG signals and converting the training analog sweat sensor signals to digital sweat sensor data; and
creating a sweat stress profile of the patient based on the digital training EEG data and the digital training sweat sensor data.

19. The non-transitory computer readable storage medium of claim 18, wherein the stressors are introduced via at least one of: (i) a virtual reality (VR) interface of the computer device, (ii) an augmented reality (AR) interface of the computing device, (iii) a control of an ambient temperature of the controlled environment, (iv) a control of an ambient humidity of the controlled environment, and (v) a control of an ambient air-flow of the controlled environment.

20. The non-transitory computer readable storage medium of claim 11, wherein the analog EEG signals and the analog sweat sensor signals are received wirelessly and in real time by the computer device, via a short range wireless communication technology.

* * * * *